(12) United States Patent
Farago et al.

(10) Patent No.: US 12,721,691 B2
(45) Date of Patent: Sep. 1, 2026

(54) THROMBECTOMY SYSTEM WITH LOADING BAY DOORS

(71) Applicant: Boston Scientific Scimed, Inc., Maple Grove, MN (US)

(72) Inventors: Laszlo Trent Farago, Hudson, WI (US); Jason W. Sprain, Shoreview, MN (US); Ted Jerome Perron, White Bear Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 247 days.

(21) Appl. No.: 18/604,956

(22) Filed: Mar. 14, 2024

(65) Prior Publication Data

US 2024/0307144 A1 Sep. 19, 2024

Related U.S. Application Data

(60) Provisional application No. 63/452,517, filed on Mar. 16, 2023.

(51) Int. Cl.
*A61B 50/13* (2016.01)
*A61B 50/10* (2016.01)

(52) U.S. Cl.
CPC ........ *A61B 50/13* (2016.02); *A61B 2050/105* (2016.02)

(58) Field of Classification Search
CPC . E05F 15/16; E05F 15/60; E05F 15/63; E05F 11/16; E05D 15/30; E05D 15/264;
(Continued)

(56) References Cited

U.S. PATENT DOCUMENTS 2,568,566 A 9/1951 Sokolik
4,346,931 A * 8/1982 Merkle .................. B61D 19/02 160/199
(Continued)

FOREIGN PATENT DOCUMENTS

CN 115192125 A * 10/2022 ............. A61B 17/22
EP 2273942 A1 11/2009
(Continued)

OTHER PUBLICATIONS

International Search Report and Written Opinion for International Application No. PCT/US2024/019892, dated Jul. 11, 2024. (12 pages).

*Primary Examiner* — Hiwot E Tefera
(74) *Attorney, Agent, or Firm* — Seager Tufte & Wickhem, LLP

(57) ABSTRACT

Thrombectomy systems including a console having loading bay doors. An illustrative console may comprise a plurality of removable panels enclosing the internal structure of the console, at least one door assembly, a carriage assembly configured to receive a pump/catheter assembly and disposed within the interior of the console and accessible via the at least one door assembly, and at least one linear actuator coupled to the at least one door assembly. The at least one door assembly may be movable between an open configuration configured to expose an interior of the console and a closed configuration configured to enclose the interior of the console. Linear movement of the at least one linear actuator may be translated to rotational movement of the at least one door assembly.

20 Claims, 9 Drawing Sheets

(58) Field of Classification Search
CPC ... E05D 15/54; A61B 50/13; A61B 2050/105; E05Y 2201/216; E05Y 2201/236
USPC .................................. 49/339, 340, 344, 345
See application file for complete search history.

(56) References Cited

U.S. PATENT DOCUMENTS 5,370,609 A 12/1994 Drasler et al.
5,425,723 A 6/1995 Wang
5,785,675 A 7/1998 Drasler et al.
5,976,103 A 11/1999 Martin
5,989,210 A 11/1999 Morris et al.
5,989,271 A 11/1999 Bonnette et al.
6,096,001 A 8/2000 Drasler et al.
6,129,697 A 10/2000 Drasler et al.
6,138,412 A * 10/2000 Rieckmann ............ E05F 15/53 49/340
6,224,570 B1 5/2001 Le et al.
6,258,061 B1 7/2001 Drasler et al.
6,471,683 B2 10/2002 Drasler et al.
6,544,209 B1 4/2003 Drasler et al.
6,558,366 B1 5/2003 Drasler et al.
6,676,627 B1 1/2004 Bonnette et al.
6,676,637 B1 1/2004 Bonnette et al.
6,719,718 B2 4/2004 Bonnette et al.
6,755,803 B1 6/2004 Le et al.
6,764,483 B1 7/2004 Bonnette et al.
6,805,684 B2 10/2004 Bonnette et al.
6,875,193 B1 4/2005 Bonnette et al.
6,926,726 B2 8/2005 Drasler et al.
6,932,828 B2 8/2005 Bonnette et al.
6,945,951 B1 9/2005 Bonnette et al.
6,984,239 B1 1/2006 Drasler et al.
7,220,269 B1 5/2007 Ansel et al.
7,226,433 B2 6/2007 Bonnette et al.
7,572,244 B2 8/2009 Weisel et al.
7,615,031 B2 11/2009 Bonnette et al.
7,842,010 B2 11/2010 Bonnette et al.
7,846,175 B2 12/2010 Bonnette et al.
7,879,022 B2 2/2011 Bonnette et al.
7,935,077 B2 5/2011 Thor et al.
7,951,161 B2 5/2011 Bonnette et al.
7,996,974 B2 8/2011 Kozak et al.
8,012,117 B2 9/2011 Bonnette et al.
8,162,877 B2 4/2012 Bonnette et al.
8,162,878 B2 4/2012 Bonnette et al.
8,171,673 B2 * 5/2012 Helms .................. E05F 15/622 49/502
8,303,538 B2 11/2012 Bonnette et al.
8,353,858 B2 1/2013 Kozak et al.
8,430,837 B2 4/2013 Jenson et al.
8,439,878 B2 5/2013 Bonnette et al.
8,475,487 B2 7/2013 Bonnette et al.
8,491,523 B2 7/2013 Scherger, III et al.
8,597,238 B2 12/2013 Bonnette et al.
8,647,294 B2 2/2014 Bonnette et al.
8,657,777 B2 2/2014 Kozak et al.
8,827,041 B2 * 9/2014 Brown ................. E05F 1/1066 187/337
8,900,179 B2 12/2014 Jenson et al.
8,998,843 B2 4/2015 Bonnette et al.
9,078,691 B2 7/2015 Morris et al.
9,510,854 B2 12/2016 Mallaby
9,662,137 B2 5/2017 Jenson et al.
9,833,257 B2 12/2017 Bonnette et al.
9,883,877 B2 2/2018 Look et al.
10,004,846 B2 6/2018 Bonnette et al.
10,314,608 B2 6/2019 Jenson et al.
10,492,805 B2 12/2019 Culbert et al.
10,499,944 B2 12/2019 Mallaby
10,561,440 B2 2/2020 Look et al.
10,632,245 B2 4/2020 Eubanks et al.
10,716,583 B2 7/2020 Look et al.
2003/0010142 A1 1/2003 Pedemonte
2005/0096607 A1 5/2005 Beck
2006/0103089 A1 * 5/2006 Decoste ................ A47B 19/00 280/47.34
2006/0106285 A1 5/2006 Boulais et al.
2006/0129091 A1 6/2006 Bonnette et al.
2007/0073233 A1 * 3/2007 Thor ................ A61M 25/0122 606/167
2008/0188793 A1 8/2008 Kozak et al.
2008/0275383 A1 11/2008 Weisel et al.
2008/0319386 A1 12/2008 Bonnette et al.
2011/0015564 A1 1/2011 Bonnette et al.
2011/0094160 A1 * 4/2011 Houser .................. E05F 15/63 49/31
2012/0110910 A1 * 5/2012 Neff ......................... E05F 3/02 49/358
2013/0008917 A1 * 1/2013 Huang ................... E06B 3/483 49/358
2013/0046282 A1 2/2013 O'Day et al.
2013/0212948 A1 * 8/2013 Nixon .................. E05F 15/643 49/360
2013/0310845 A1 11/2013 Scherger, III et al.
2014/0005699 A1 1/2014 Bonnette et al.
2014/0020298 A1 * 1/2014 Kowalczyk ............ E05D 15/54 49/366
2014/0088610 A1 3/2014 Bonnette et al.
2014/0145576 A1 * 5/2014 White .................. E05F 1/1253 312/319.1
2014/0214060 A1 7/2014 Bonnette et al.
2014/0228869 A1 8/2014 Bonnette et al.
2014/0277006 A1 9/2014 Bonnette et al.
2016/0030858 A1 2/2016 Giacomini
2018/0126830 A1 * 5/2018 Lampsa ................... E05D 3/08
2018/0207397 A1 7/2018 Look et al.
2018/0228502 A1 8/2018 Shaffer et al.
2019/0209745 A1 7/2019 Hanson et al.
2019/0274704 A1 9/2019 Jenson et al.
2020/0015840 A1 1/2020 Mallaby
2020/0022711 A1 1/2020 Look et al.
2020/0121356 A1 4/2020 Look et al.
2020/0155178 A1 5/2020 Culbert et al.
2020/0297363 A1 9/2020 Look et al.
2020/0347670 A1 * 11/2020 Kwon .................. A47F 3/0478
2021/0189784 A1 * 6/2021 Dal Canale .......... B23Q 1/5468
2023/0212902 A1 * 7/2023 Lee ...................... E05F 15/611 49/334
2023/0228143 A1 * 7/2023 Stern ...................... E05B 17/10 49/27

FOREIGN PATENT DOCUMENTS

EP 2362751 B1 9/2016
EP 2120737 B1 4/2020
EP 3689274 A1 8/2020
EP 3145557 B1 1/2021
EP 3821921 A1 5/2021
EP 3570901 B1 5/2022
JP 5385155 B2 1/2014
WO 0151116 A2 7/2001
WO 2008097993 A2 8/2008
WO 2017041062 A1 3/2017
WO 2017177022 A1 10/2017
WO 2019140132 A1 7/2019

* cited by examiner

THROMBECTOMY SYSTEM WITH LOADING BAY DOORS

CROSS-REFERENCE TO RELATED APPLICATIONS

This application claims the benefit of U.S. Provisional Patent Application Ser. No. 63/452,517, filed Mar. 16, 2023, which is incorporated herein by reference.

TECHNICAL FIELD

The disclosure is directed to thrombectomy systems. More particularly, the disclosure is directed to a thrombectomy system with doors for enclosing portions of the catheter system.

BACKGROUND

Thrombectomy is a procedure for removing thrombus from the vasculature of a patient. Mechanical and fluid-based systems can be used to remove thrombus. With fluid-based systems, an infusion fluid may be infused to a treatment area of a vessel with a catheter to dislodge the thrombus. In some instances, an effluent (e.g., the infusion fluid and/or blood) including the dislodged thrombus may be extracted from the vessel through the catheter. Of the known thrombectomy systems and methods, there is an ongoing need to provide alternative configurations of thrombectomy catheters and systems, as well as methods of operating such thrombectomy systems.

SUMMARY

This disclosure provides design, material, manufacturing method, and use alternatives for medical devices.

In a first example, a console for a thrombectomy system may comprise one or more panels enclosing an internal structure of the console, at least one door assembly, the at least one door assembly movable between an open configuration configured to expose an interior of the console and a closed configuration configured to enclose the interior of the console, a carriage assembly disposed within the interior of the console and accessible via the at least one door assembly, the carriage assembly configured to receive a pump/catheter assembly, and at least one linear actuator coupled to the at least one door assembly. Linear movement of the at least one linear actuator may be translated to rotational movement of the at least one door assembly.

Alternatively or additionally to any of the examples above, in another example, the at least one first door assembly may be configured to open into the interior of console.

Alternatively or additionally to any of the examples above, in another example, the at least one door assembly may be configured to rotate about an outer lateral side thereof.

Alternatively or additionally to any of the examples above, in another example, the at least one door assembly may comprise a door panel and a first door attachment bracket. The first door attachment bracket may be coupled to a first end of the door panel.

Alternatively or additionally to any of the examples above, in another example, the console may further comprise a fixation member coupled to the first door attachment bracket. The fixation member may be configured to be rotatably coupled to a frame of the console.

Alternatively or additionally to any of the examples above, in another example, the console may further comprise a drive hinge coupled to a second end of the door panel.

Alternatively or additionally to any of the examples above, in another example, the drive hinge may be coupled to a bell crank system. The bell crank system may be coupled to the at least one linear actuator.

Alternatively or additionally to any of the examples above, in another example, the bell crank system may comprise a second door attachment bracket, an arm extending radially from the second door attachment bracket, and an actuator rod coupled to the arm.

Alternatively or additionally to any of the examples above, in another example, the console may further comprise at least one magnet disposed adjacent to a first end of the at least one door assembly.

Alternatively or additionally to any of the examples above, in another example, the at least one door assembly may comprise a first door assembly and a second door assembly.

Alternatively or additionally to any of the examples above, in another example, the at least one linear actuator may comprise a first linear actuator coupled to the first door assembly and a second linear actuator coupled to the second door assembly.

Alternatively or additionally to any of the examples above, in another example, the first door assembly and the second door assembly may be configured to be independently operated.

Alternatively or additionally to any of the examples above, in another example, the first door assembly and the second door assembly may be configured to be simultaneously operated.

Alternatively or additionally to any of the examples above, in another example, when the first door assembly and the second door assembly are in the closed configuration, the first door assembly and the second door assembly may define an opening configured to allow a portion of a pump/catheter assembly to pass therethrough.

Alternatively or additionally to any of the examples above, in another example, the console may further comprise a control panel.

Alternatively or additionally to any of the examples above, in another example, the at least one first door assembly may include a first door assembly and a second door assembly, wherein both the first door assembly and the second door assembly may be configured to open into the interior of console.

In another example, a console for a thrombectomy system may comprise a plurality of panels enclosing an internal structure of the console, a first door assembly comprising a door panel, a first door attachment bracket, and a magnet disposed within a cavity of the first door attachment bracket, a second door assembly comprising a door panel, a first door attachment bracket, and a magnet disposed within a cavity of the first door attachment bracket, a first linear actuator coupled to the first door assembly, a second linear actuator coupled to the second door assembly, and a carriage assembly disposed within the interior of the console and accessible via the first door assembly and the second door assembly. The carriage assembly may be configured to receive a pump/catheter assembly. The first linear actuator may be configured to move the first door assembly between an open configuration configured to expose an interior of the console and a closed configuration configured to enclose the interior of the console and the second linear actuator may be configured to move the second door assembly between an open configuration configured to expose an interior of the console and a closed configuration configured to enclose the interior of the console.

Alternatively or additionally to any of the examples above, in another example, the first linear actuator may be coupled to the first door assembly via a first bell crank assembly and the second linear actuator may be coupled to the second door assembly via a second bell crank assembly.

Alternatively or additionally to any of the examples above, in another example, the first bell crank assembly and the second bell crank assembly may each comprise a second door attachment bracket, an arm extending radially from the second door attachment bracket, and an actuator rod coupled to the arm.

Alternatively or additionally to any of the examples above, in another example, the console may further comprise a first drive hinge extending between the first door panel and the first bell crank assembly and a second drive hinge extending between the second door panel and the second bell crank assembly.

In another example, a console for a thrombectomy system a housing enclosing an internal structure of the console, a first door assembly comprising a door panel and a first door attachment bracket, a second door assembly comprising a door panel and a first door attachment bracket, a first linear actuator coupled to the first door assembly, a second linear actuator coupled to the second door assembly, and a carriage assembly disposed within the interior of the console and accessible via the first door assembly and the second door assembly, the carriage assembly configured to receive a pump/catheter assembly. The first door assembly and the second door assembly may each be movable between an open configuration configured to expose an interior of the console and a closed configuration configured to enclose the interior of the console. The first door assembly and the second door assembly may be configured to be moved independently or simultaneously.

The above summary of some example embodiments is not intended to describe each disclosed embodiment or every implementation of the disclosure.

BRIEF DESCRIPTION OF THE DRAWINGS

The disclosure may be more completely understood in consideration of the following detailed description of various embodiments in connection with the accompanying drawings, in which.

Figure 1:
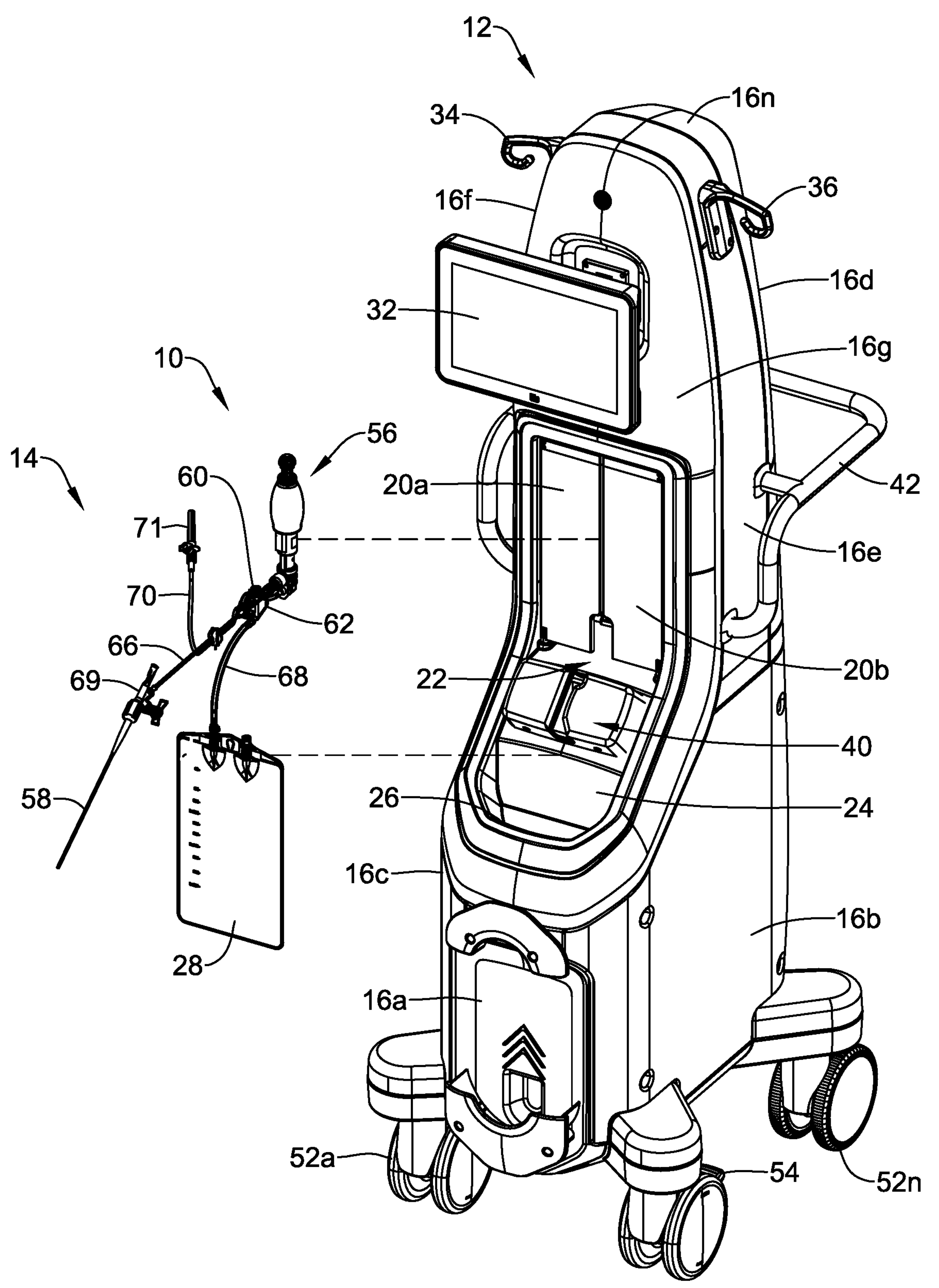
FIG. 1 is a perspective view of an illustrative thrombectomy system.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

All numeric values are herein assumed to be modified by the term "about", whether or not explicitly indicated. The term "about" generally refers to a range of numbers that one of skill in the art would consider equivalent to the recited value (e.g., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Thrombectomy catheters and systems may be used to remove thrombus, plaques, lesions, clots, etc. from veins or arteries. The control console or drive unit of a thrombectomy system may enclose portions of the thrombectomy catheter. Doors may be provided which are selectively opened to allow the user to place the single use device within the loading bay of a console and closed to allow for the safe operation of the system. Disclosed herein is a loading bay door system which allows for greater user control and increased safety.

FIG. 1 is a perspective view of an illustrative thrombectomy system 10. The thrombectomy system 10 may include a control console 12, including a drive unit, and a pump/catheter assembly 14. In some instances, the pump/catheter assembly 14 may be a single use device in which a new pump/catheter assembly 14 may be used with the console 12 for each medical procedure. The console 12 may include a housing enclosing the internal structure of the console 12. Shown on the console 12 are a plurality of removable panels **16*a*-16*n* about and along the console 12 enclosing the internal structure of the console 12. An illustrative console 12 is described in commonly assigned U.S. Pat. No. 7,935, 077, titled THROMBECTOMY CATHETER DEPLOYMENT SYSTEM, the disclosure of which is hereby incorporated by reference. Centrally located in the console 12 and aligned to the lower region of the panel 16***g* may be automatically opening loading bay door assemblies 20*a*, 20*b* which open to expose the interior of the console 12 to provide access to a carriage assembly 22. The carriage assembly 22, which may accommodate components of the pump/catheter assembly 14 is shown accessible via opening the closed door assemblies 20*a*, 20*b*. The console 12 may include a catch basin for collecting fluid leakage from the components of the pump/catheter assembly 14. For example, a drip tray 24 is shown located on the front of the console 12 extending from below the carriage assembly 22 toward the panel 16*a*. In some instances, the drip tray 24 may be removable. Other configurations of catch basins are also contemplated. The drip tray 24 and/or a receptacle 26 may collectively support and accommodate an effluent collection bag, such as effluent collection bag 28 of the pump/catheter assembly 14. In other instances, the console 12 may include a different structure, such as a hook for hanging the effluent collection bag 28 from, or a shelf for setting the effluent collection bag 28 on. The effluent waste tube 68 may also be positioned in the roller pump 40 between the tube guides with the effluent collection bag 28 connected to the effluent waste tube 68. The effluent collection bag 28 may be suitably positioned for collecting effluent during the medical procedure. Pump rollers (not shown) of the roller pump 40 may rotatably engage the effluent waste tube 68 to control effluent fluid flow through the effluent waste tube 68 to the effluent collection bag 28.

In instances where the carriage assembly 22 is movable, a carriage assembly activation switch (not explicitly shown) may be provided with the console 12, such as located on panel 16*g*, to selectively position the carriage assembly 22 inwardly or outwardly. In other instances, the carriage assembly 22 may be positioned using a control panel and/or user interface 32. A user interface 32, including memory and/or processing capabilities, may be provided with the console 12, such as located at the upper region of the console 12 between the upper regions of the upper side panels 16*e* and 16*f*. The user interface 32 may be a guided user interface (GUI) including a touch screen display to allow a user to provide input to the user interface 32 and view information on a same display screen. However, this is not required. In other instances, the user input may be separate from the display screen. Saline bag hooks 34 and 36 may extend through the panels 16*e* and 16*f* to hang saline bags therefrom. The console 12 may include a handle 42 as well as a plurality of wheels 52*a*-52*n* and brake pedals 54 for wheel lockage to assist in maneuvering the console 12 by medical personnel.

The pump/catheter assembly 14, which may be a disposable single-use device, is shown unattached from the console 12. The pump/catheter assembly 14 includes a pump 56 and a thrombectomy catheter 58. During use, a portion of the pump/catheter assembly 14 may be secured within a portion of the console 12. Other components included in the pump/catheter assembly 14 may include a bubble trap 60 attached to the pump 56, a connection manifold assembly 62 connected to the bubble trap 60, an effluent return tube 66 connected between the connection manifold assembly 62 and the thrombectomy catheter 58, a high-pressure fluid supply tube (not explicitly shown) attached between the output of the pump 56 and the thrombectomy catheter 58 which may be coaxially arranged inside the effluent return tube 66, a transition fixture 69 between the distal end of the effluent return tube 66 and the proximal end of the thrombectomy catheter 58, an effluent waste tube 68 connecting the effluent collection bag 28 to the connection manifold assembly 62, and a fluid supply tube 70 having a bag spike 71 connecting a fluid supply bag (e.g., a saline bag) to the connection manifold assembly 62. The fluid supply tube 70 may be in fluid communication with the interior of the bubble trap 60 to provide fluid from the fluid supply bag to the pump 56 and then to the thrombectomy catheter 58 through the high-pressure fluid supply tube.

Figure 2:
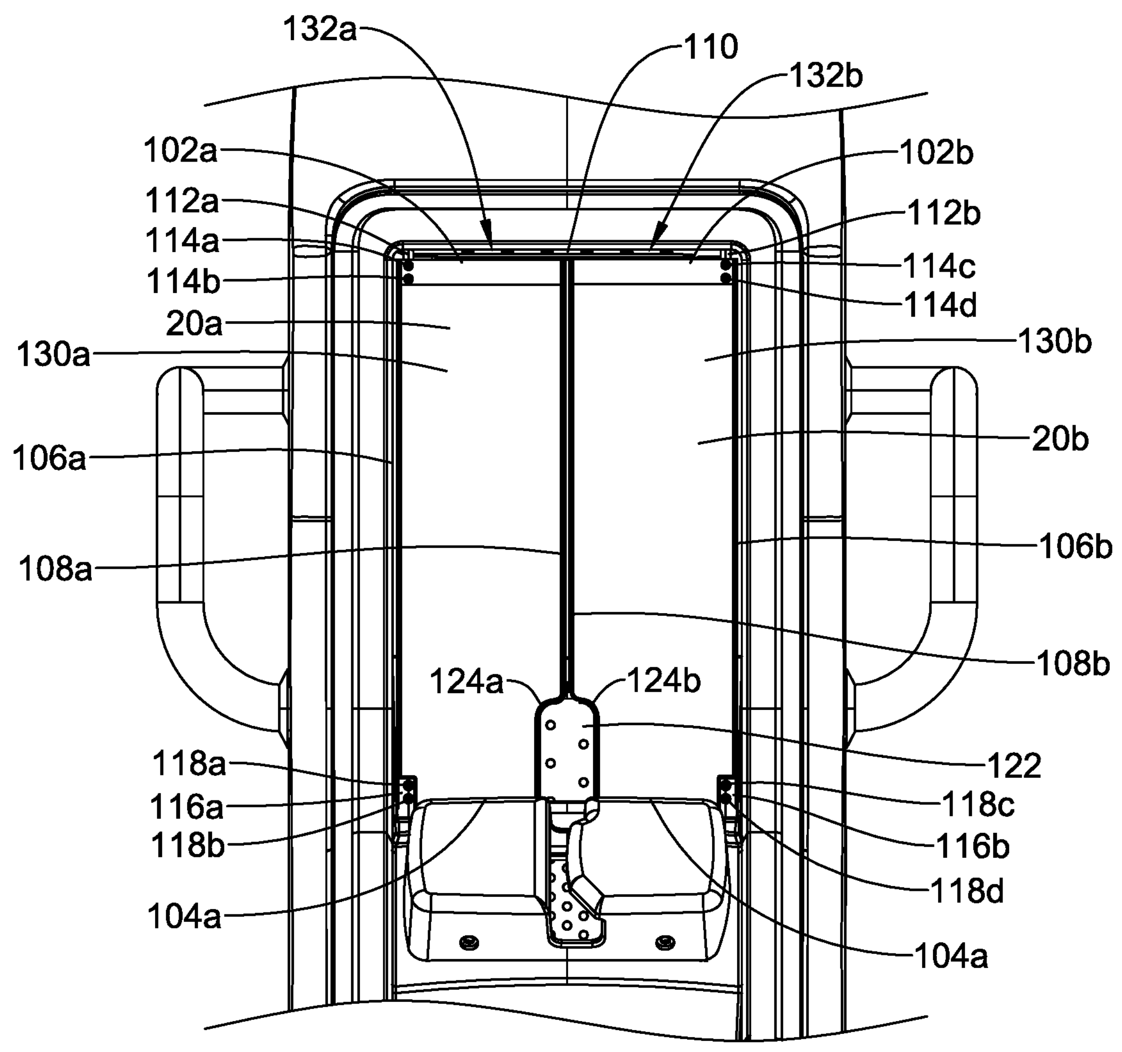
FIG. 2 is a front view of an illustrative thrombectomy console with the doors in a closed configuration.

FIG. 2 is a front view of an upper portion of the console 12 with the door assemblies 20*a*, 20*b* in a closed configuration. Each door assembly 20*a*, 20*b* may include a first end 102*a*, 102*b*, a second end 104*a*, 104*b*, an outer lateral side 106*a*, 106*b*, and an inner lateral side 108*a*, 108*b*. The outer lateral sides 106*a*, 106*b* and inner laterals sides 108*a*, 108*b* may each extend from the first end 102*a*, 102*b* to the second end 104*a*, 104*b*. Each door 30 assembly 20*a*, 20*b* may each be pivotably coupled to a frame 110 of the console 12 adjacent to the outer lateral side 106*a*, 106*b* thereof. For example, the first door assembly 20*a* may include a pin 112*a* fixedly coupled adjacent to the first end 102*a* and the outer lateral side 106*a* via one or more fixation members 114*a*, 114*b*, such as, but not limited to set screws, screws, bolts, rivets, etc. The pin 112*a* may extend away from the first end 102*a* of the first door assembly 20*a* in a direction opposite from the second end 104*a*. The pin 112*a* may be rotatably received within an opening or aperture 129*a* (see, for example, FIG. 3) of the frame 110. Thus, the pin 112*a* may be configured to rotate as the first door assembly 20*a* pivots between an open configuration (FIG. 3) and a closed configuration (FIG. 2). Similarly, the second door assembly 20*b* may include a pin 112*b* fixedly coupled adjacent to the first end 102*b* and the outer lateral side 106*b* via one or more fixation members 114*c*, 114*d*, such as, but not limited to set screws, screws, bolts, pins, etc. The pin 112*b* may extend away from the first end 102*b* of the door assembly 20*b* in a direction opposite from the second end 104*b*. The pin 112*b* may be rotatably received within an opening or aperture 129*b* (see, for example, FIG. 3) of the frame 110. Thus, the pin 112*b* may be configured to rotate as the second door assembly 20*b* pivots between an open configuration (FIG. 3) and a closed configuration (FIG. 2).

The first door assembly 20*a* may also be fixedly coupled to a drive hinge 116*a* adjacent to the second end 104*a* and the outer lateral side 106*a* thereof via one or more fixation members 118*a*, 118*b*, such as, but not limited to, set screws, screws, bolts, pins, etc. As will be described in more detail herein, the drive hinge 116*a* may be coupled to an actuation assembly 120*a* (see, for example, FIG. 3) configured to move the first door assembly 20*a* between a closed configuration and an open configuration. Similarly, the second door assembly 20*b* may also be fixedly coupled to a drive hinge 116*b* adjacent to the second end 104*b* and the outer lateral side 106*b* thereof via one or more fixation members 118*b*, 118*b*, such as, but not limited to, set screws, screws, bolts, pins, etc. As will be described in more detail herein, the drive hinge 116*b* may be coupled to an actuation assembly 120*b* (see, for example, FIG. 3) configured to move the door assembly 20*b* between a closed configuration and an open configuration.

The width of the door assemblies 20*a*, 20*b* may be smaller adjacent to the second end 104*a*, 104*b* thereof than a width of the door assemblies 20*a*, 20*b* adjacent to the first end 102*a*, 102*b* thereof. For example, the width of the door assemblies 20*a*, 20*b* may transition from the first width to the second smaller width at a curved region 124*a*, 124*b* of the inner lateral sides 108*a*, 108*b*. The first and second door assemblies 20*a*, 20*b* may be mirror images of one another such that the curved regions 124*a*, 124*b* are positioned at similar axial locations. The reduction in the width of the door assemblies 20*a*, 20*b* may define an opening 122 for allowing components of the thrombectomy catheter 58 to extend between an interior or loading bay 38 (FIG. 3) of the console 12 and an exterior of the console 12. It is further contemplated that the opening 122 may be sized and shaped to allow the door assemblies 20*a*, 20*b* to be opened and closed when a pump/catheter assembly 14 is assembled with the carriage assembly 22.

Figure 3:
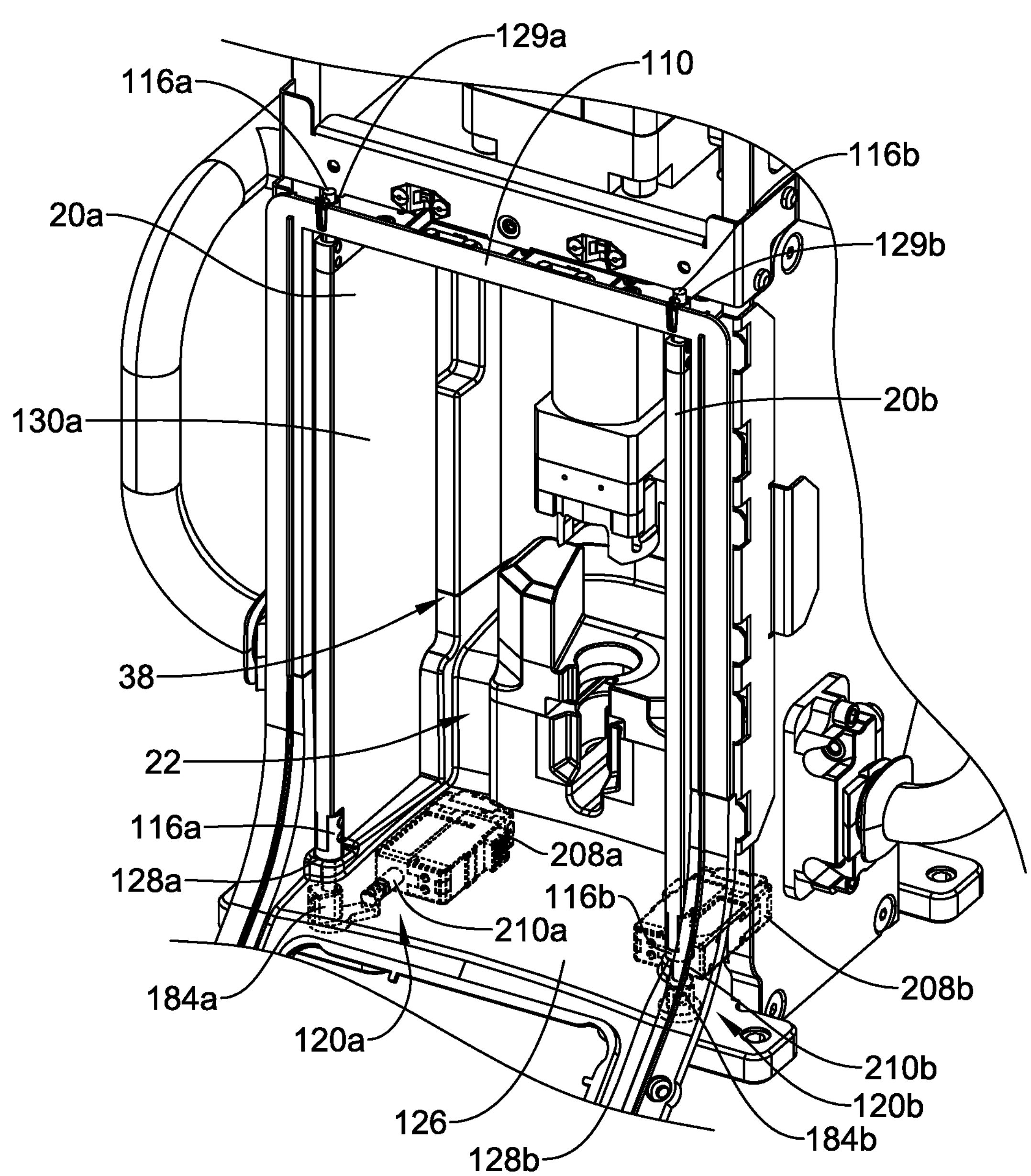
FIG. 3 is a perspective view of a portion of the thrombectomy console with the door assemblies in an open configuration.

FIG. 3 is a perspective view of a portion of the console 12 with the door assemblies 20*a*, 20*b* in an open configuration. The door assemblies 20*a*, 20*b* may each be configured to rotate or hinge inward about an axis that extends through the pin 112*a*, 112*b* and the drive hinge 116*a*, 116*b* into a loading bay or interior 38. This may locate any pinch points within the loading bay or interior 38 providing pinch point protection to the user. It is further contemplated that inwardly opening door assemblies 20*a*, 20*b* may allow for better user access to the loading bay 38 of the console 12. In some examples, the interior walls of the console 12 may include recesses sized and shaped to allow the door assemblies 20*a*, 20*b* to be positioned therein when the door assemblies are in the open configuration. While the door assemblies 20*a*, 20*b* are described as rotating into the loading bay 38 as they open, it is contemplated that in some cases, the door assemblies 20*a*, 20*b* may rotate away from the loading bay 38, or outward, as they open.

As described above, the drive hinges 116*a*, 116*b* may each be coupled to an individual actuation assembly 120*a*, 120*b*. This may allow the door assemblies 20*a*, 20*b* to be operated individually or substantially simultaneously, as will be described in more detail herein. The drive hinges 116*a*, 116*b* may pass through apertures 128*a*, 128*b* extending though a bottom surface 126 of the frame 110. A portion of the drive hinge 116*a*, 116*b* may be coupled to the actuation assembly 120*a*, 120*b*.

Figure 4A:
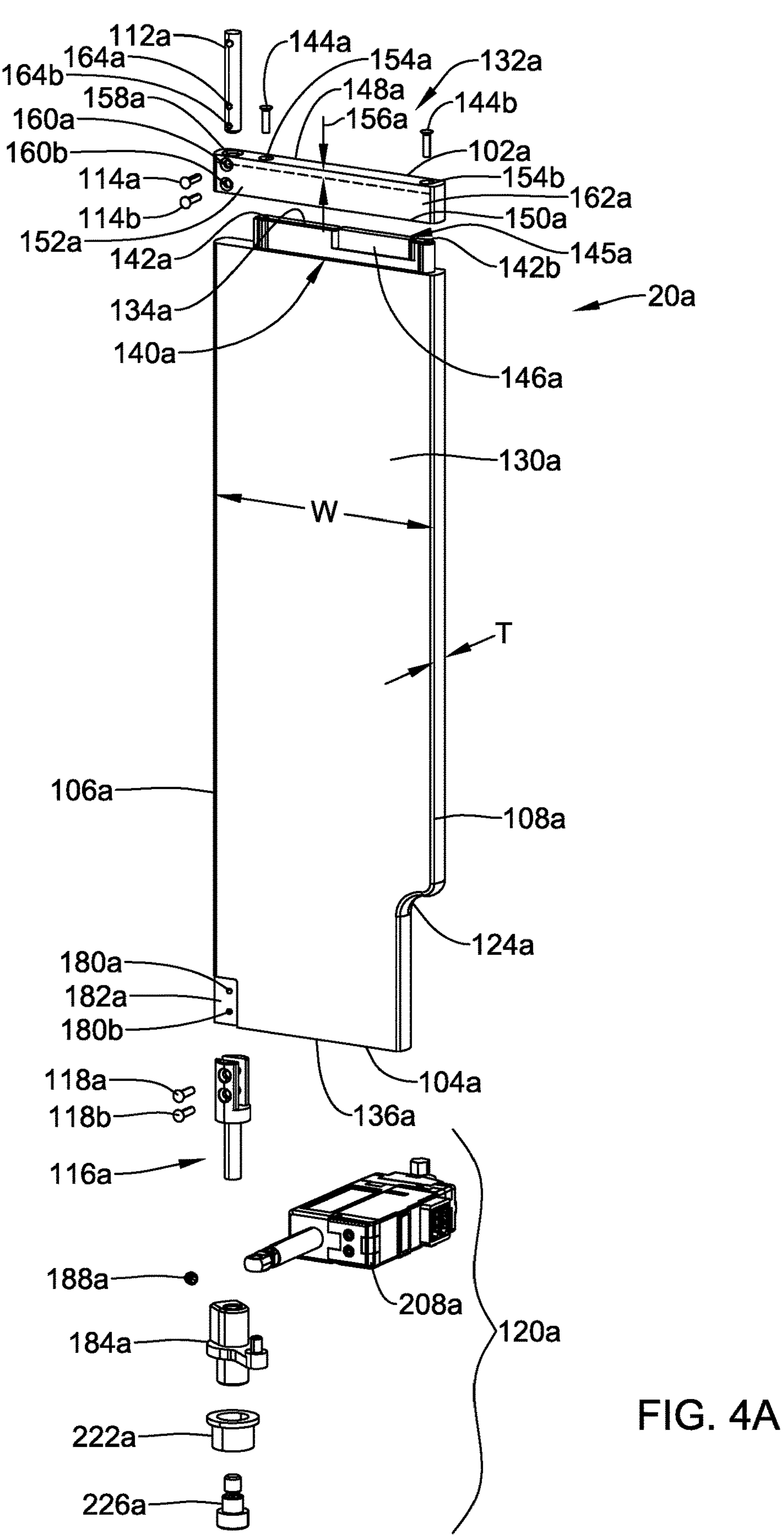
FIG. 4A is an exploded perspective view of the first door assembly and the first actuation assembly.

FIG. 4A is an exploded perspective view of the first door assembly 20*a* and the first actuation assembly 120*a*. It should be understood that the second door assembly 20*b* and the second actuation assembly 120*b* include all of the same components as the first door assembly 20*a* and the first actuation assembly 120*a* in a mirror image configuration. The first door assembly 20*a* may include a door panel 130*a* and a first door attachment bracket 132*a*. The first door attachment bracket 132*a* may include the pin 112*a* for hingedly coupling the door assembly 20*a* to the console 12 as well as one or more fixation members. The first door attachment bracket 132*a* may have a width and thickness similar to a width W and thickness T of the door panel 130*a*. The door panel 130*a* may extend from a first end 134*a* to a second end 136*a*. In some examples, the door panel 130*a* may include a first end region 140*a* that has a reduced width and thickness than the width W and thickness T of an intermediate region of the door panel 130*a*. This may allow the first door attachment bracket 132*a* to be disposed over the first end region 140*a* of the door panel 130*a* while maintaining relatively uniform outer dimensions of the door assembly 20*a*. The first end region 140*a* of the door panel 130*a* may include a first aperture 142*a* and a second aperture 142*b* each for receiving a fixation member 144*a*, 144*b* therein. The fixation members 144*a*, 144*b* may include, but are not limited to set screws, screws, bolts, pins, etc. Generally, the fixation members 144*a*, 144*b* may be configured to secure the first door attachment bracket 132*a* to the door panel 130*a*. The first end region 140*a* of the door panel 130*a* may further include a magnet 146*a* disposed within a recess 145*a* formed in the first end region 140*a*. A hall effect sensor (not explicitly shown) may be positioned in the frame 110 of the console 12 adjacent to the magnet 146*a* when the door assembly 20*a* is in the closed configuration. The hall effect sensor may detect the presence of the magnet 146*a* to determine whether the door assembly 20*a* is open or closed. It is contemplated that a procedure may not begin until both door assemblies 20*a*, 20*b* are in the closed configuration.

The door attachment bracket 132*a* may be secured to the door panel 130*a* adjacent to a first end 134*a* of the door panel 130*a*. The first door attachment bracket 132*a* may extend from a first generally closed end 148*a* to a second generally open end 150*a*. For example, the second end 150*a* may be configured to be disposed over the first end region 140*a* of the door panel 130*a*. For example, the first door attachment bracket 132*a* may include a cavity 152*a* extending from the second end 150*a* towards the first end 148*a*, but not extending through an entirety of the height of the first door attachment bracket 132*a*. When the first door attachment bracket 132*a* is assembled with the door panel 130*a*, the first door attachment bracket 132*a* may be secured to the door panel 130*a* via the one or more fixation members 144*a*, 144*b*. For example, the fixation members 144*a*, 144*b* may extend through a first aperture 154*a* and a second aperture 154*b* of the first door attachment bracket 132*a*, respectively. The first and second apertures 154*a*, 154*b* may extend from the first end 148*a* and through a wall 156*a* thereof. The fixation members 144*a*, 144*b* may also extend into the apertures 142*a*, 142*b* at the first end 134*a* of the door panel 130*a*. When the first door attachment bracket 132*a* is assembled with the door panel 130*a*, the magnet 146*a* may be disposed within the cavity 152*a* of the first door attachment bracket 132*a*.

The first door attachment bracket 132*a* may further include a through hole or aperture 158*a* extending from the first end 148*a* to the second end 150*a*. The through hole 158*a* may be configured to receive the pin 112*a* therein. The first door attachment bracket 132*a* may further include a third aperture 160*a* and a fourth aperture 160*b* extending through a front surface 162*a* thereof. The third and fourth apertures 160*a*, 160*b* may extend through the front surface 162*a* adjacent to the through hole 158*a*. The third and fourth apertures 160*a*, 160*b* may be configured to receive the fixation members 114*a*, 114*b* to fixedly couple the pin 112*a* to the first door attachment bracket 132*a* and thus the first door assembly 20*a*. It is contemplated that the fixation members 114*a*, 114*b* may be configured to engage apertures 164*a*, 164*b* formed in a second end region of the pin 112*a*. Alternatively, the fixation members 114*a*, 114*b* may be configured to frictionally engage an outer surface of the pin 112*a*.

Figure 4B:
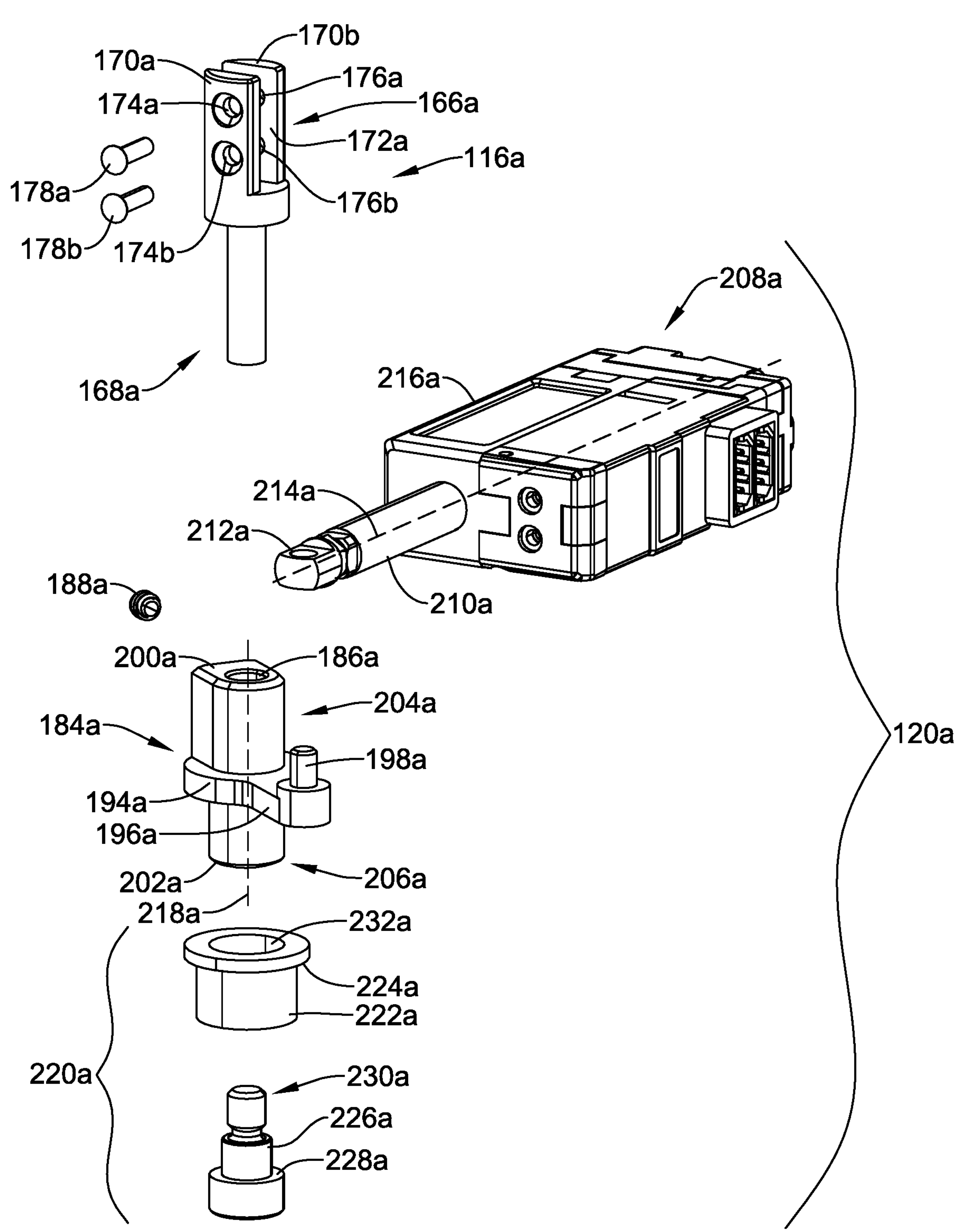
FIG. 4B is an enlarged exploded front perspective view of the drive hinge and the actuation assembly.
Figure 4C:
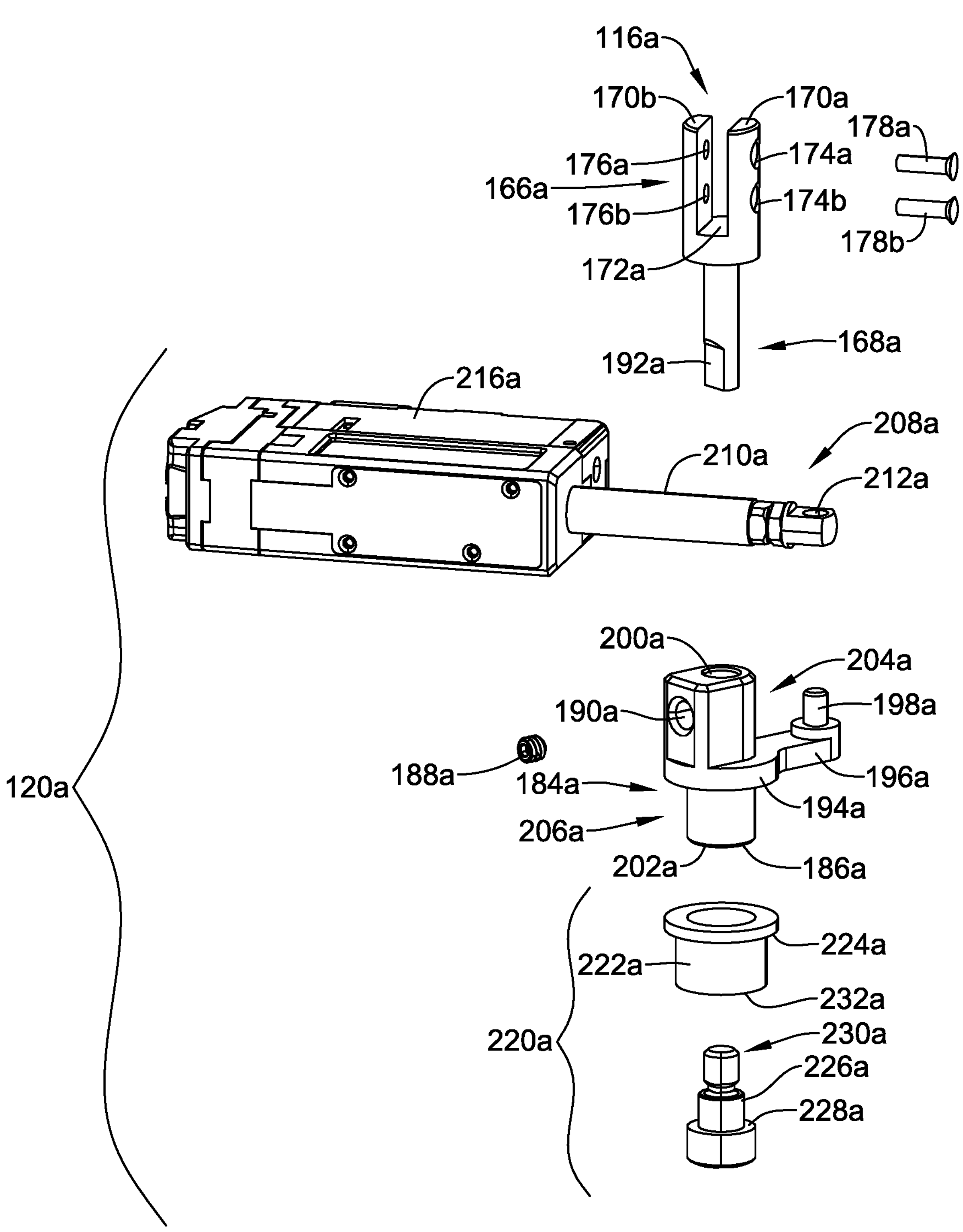
FIG. 4C is an enlarged exploded side perspective view of the drive hinge and the actuation assembly.

The drive hinge 116*a* may be secured to the door panel 130*a* adjacent the second end 136*a* thereof. Referring additionally to FIGS. 4B and 4C which illustrate an enlarged exploded front perspective view and an enlarged exploded side perspective view, respectively, of the drive hinge 116*a* and the actuation assembly 120*a*, the drive hinge 116*a* may include a first end region 166*a* and a second end region 168*a*. The first end region 166*a* may have a generally "U" shaped configuration including a first arm 170*a*, a second arm 170*b*, and a channel 172*a* therebetween. Each arm 170*a*, 170*b* may include a first aperture 174*a*, 176*a* and a second aperture 174*b*, 176*b* extending through a thickness thereof. The first apertures 174*a*, 176*a* may each be configured to receive a first fixation member 178*a* therethrough and the second apertures 174*b*, 176*b* may each be configured to receive a first fixation member 178*b* therethrough. The fixation members 178*a*, 178*b* may be configured to extend through apertures 180*a*, 180*b* (see, for example, FIG. 4A) extending through a thickness of the door panel 130*a*. The apertures 180*a*, 180*b* may be formed through a corner of the door panel 130*a* adjacent to the outer lateral side 106*a* and the second end 104*a* of the door assembly 20*a* in a corner region 182*a* having a reduced thickness relative to the thickness T of an intermediate region of the first door panel 130*a* adjacent to the inner lateral side 108*a* and the second end 104*a* of the door assembly 20*a*. The corner region 182*a* may be sized and shaped to be assembled within the channel 172*a* of the drive hinge 116*a*. When the corner region 182*a* is assembled within the channel 172*a* of the drive hinge 116*a*, the first apertures 174*a*, 176*a* of the arms 170*a*, 170*b* may be aligned with the first aperture 180*a* of the corner region 182*a*. Similarly, the second apertures 174*b*, 176*b* of the arms 170*a*, 170*b* may be aligned with the second aperture 180*b* of the corner region 182*a*. When assembled, the fixation members 178*a*, 178*b* may be inserted into the apertures 174*a*, 174*b* of the first arm 170*a*, through the apertures 180*a*, 180*b* of the corner region 182*a*, and into the apertures 176*a*, 176*b* of the second arm 170*b* to secure the drive hinge 116*a* to the door assembly 20*a*.

The second end region 168*a* of the drive hinge 116*a* may be configured to be disposed within a lumen 186*a* of a second door attachment bracket 184*a*. The second end region 168*a* of the drive hinge 116*a* may be secured to the second door attachment bracket 184*a* via a fixation member 188*a* such as, but not limited to, a set screw, screw, bolt, pin, etc. The fixation member 188*a* may extend through an aperture 190*a* extending through a side wall of the second door attachment bracket 184*a* to the lumen 186*a* thereof to frictionally engage a flattened coupling surface 192*a* of the drive hinge 116*a*.

The second door attachment bracket 184*a* may further include radially extending region 194*a* with an arm 196*a* extending radially from the radially extending region 194*a*. The radially extending region 194*a* may be positioned between a first end 200*a* and a second end 202*a* of the second door attachment bracket 184*a*. A first end region 204*a* of the second door attachment bracket 184*a* may be disposed above the radially extending region 194*a* and a second end region 206*a* of the second door attachment bracket 184*a* may be disposed below the radially extending region 194*a*. A laterally extending protrusion or pin 198*a* may extend upwards (e.g., towards the first end 200*a* of the second door attachment bracket 184*a*) from an upper surface of the arm 196*a*. The pin 198*a* may have a longitudinal axis that extends generally parallel to a longitudinal axis 218*a* of the lumen 186*a* of the second door attachment bracket 184*a*.

The pin 198*a* may be configured to be received within a mating aperture 212*a* extending though an actuator rod 210*a* of an electric linear actuator 208*a*. Collectively, the arm 196*a*, the pin 198*a*, and the actuator rod 210*a* of the linear actuator 208*a* may form a bell crank system. The actuator rod 210*a* may be actuatable along a longitudinal axis 214*a* thereof. In the illustrated embodiment, the actuator rod 210*a* is shown in an extended configuration. In the illustrated embodiment, when the actuator rod 210*a* is in the extended configuration, the door assembly 20*a* is in the closed configuration. However, this is not required. In some cases, the door assembly 20*a* may be in the open configuration when the actuator rod 210*a* is in the extended configuration. The actuator rod 210*a* may be retracted into the housing 216*a* of the linear actuator 208*a*. As the actuator rod 210*a* is retracted into the housing 216*a* of the linear actuator 208*a*, the actuator rod 210*a* pulls the pin 198*a* and translates linear motion of the actuator rod 210*a* to rotational movement of the second door attachment bracket 184*a*. The torque is transferred to the door assembly 20*a* from the second door attachment bracket 184*a* via the drive hinge 116*a* to move the door assembly 20*a* from a closed configuration to an open configuration. For example, as the actuator rod 210*a* is actuated, the second door attachment bracket 184*a* pivots about the longitudinal axis 218*a* of the lumen 186*a* of the second door attachment bracket 184*a*. The linear actuation of the actuator rod 210*a* may be reversed to extend the actuator rod 210*a* and move the door assembly 20*a* from an open configuration to a closed configuration.

The second door attachment bracket 184*a* may be rotatably coupled to the console 12 via a coupling mechanism 220*a*. The coupling mechanism 220*a* may be configured to extend through an opening in an internal plate of the console 12 (e.g., located under the bottom surface 126 of the frame 110). Generally, a first portion 222*a* of the coupling mechanism 220*a* may include a first surface 224*a* configured to engage a first side of an internal plate of the console 12 and a second portion 226*a* of the coupling mechanism 220*a* may include a second surface 228*a* configured to engage a second side of an internal plate of the console 12. For example, the first surface 224*a* may have a greater diameter than a diameter of the opening in the internal plate of the console 12 adjacent the first side thereof. Similarly, the second surface 228*a* may have a greater diameter than a diameter of the opening in the internal plate of the console 12 adjacent the second side thereof. The diameter of the opening in the internal plate may vary along the length thereof. The internal plate of the console 12 may be positioned between the first portion 222*a* and the second portion 226*a* of the coupling mechanism 220*a*. A first end region 230*a* of the second portion 226*a* of the coupling mechanism 220*a* may be disposed within the lumen 186*a* of the second door attachment bracket 184*a*. In some cases, at least part of the first end region 230*a* may frictionally engage the inner surface of the lumen 186*a* to couple the second door attachment bracket 184*a* to the second portion 226*a* of the coupling mechanism 220*a*. Thus, the second portion 226*a* of the coupling mechanism 220*a* may rotate with the second door attachment bracket 184*a*. The second end region 206*a* of the second door attachment bracket 184*a* may be rotationally disposed within an aperture 232*a* of the first portion 222*a* of the coupling mechanism 220*a*. Thus, the first portion 222*a* of the coupling mechanism 220*a* may remain stationary as the second door attachment bracket 184*a* is rotated. Alternatively, the first portion 222*a* of the coupling mechanism 220*a* may rotate as the second door attachment bracket 184*a* is rotated.

Figure 5:
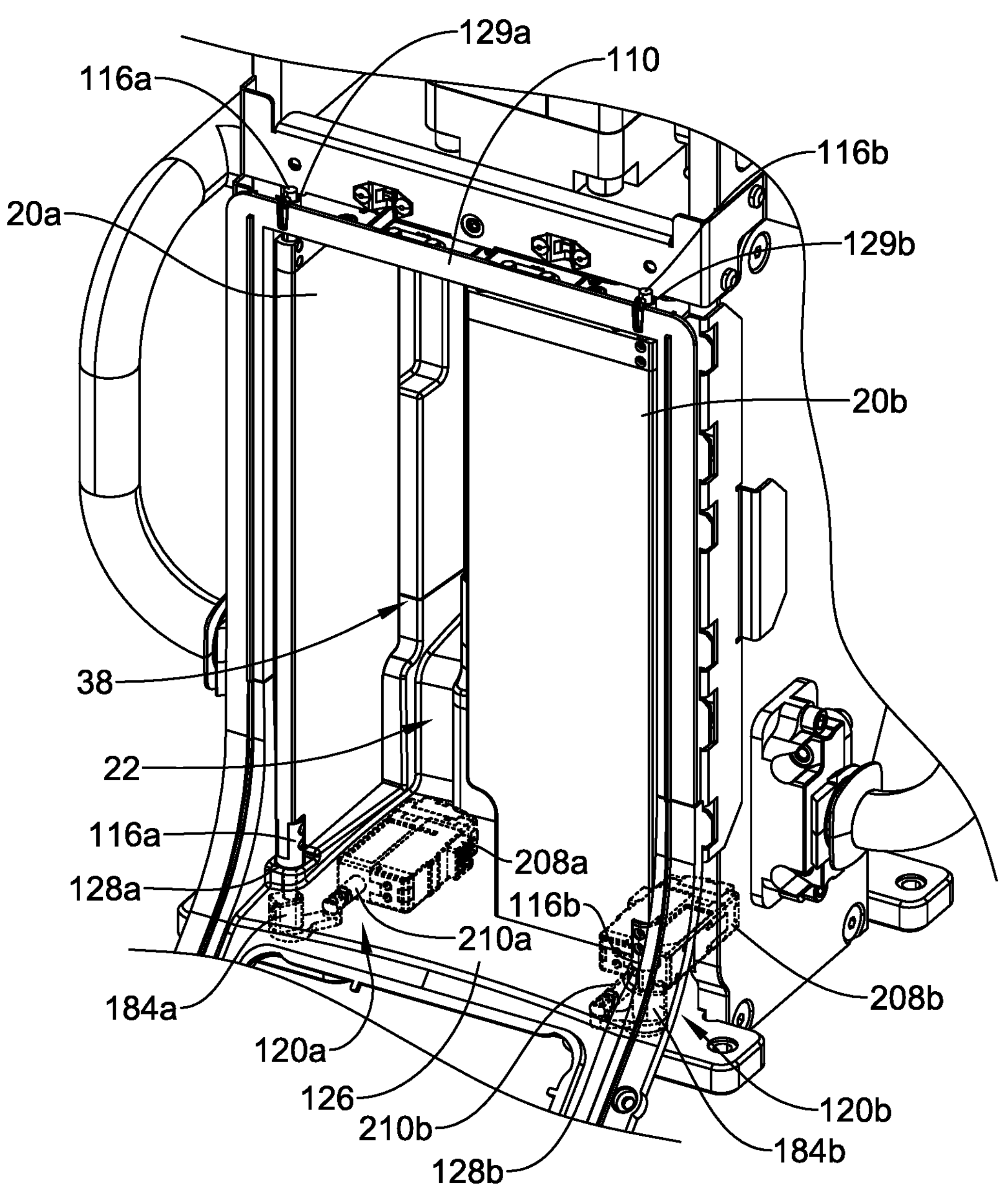
FIG. 5 is a perspective view of a portion of the thrombectomy console with the first door assembly in an open configuration and the second door assembly in a closed configuration.

FIG. 5 is a perspective view of a portion of the console 12 with the first door assembly 20*a* in an open configuration and the second door assembly 20*b* in a closed configuration. The door assemblies 20*a*, 20*b* may each be coupled to their own respective actuation assemblies 120*a*, 120*b*. Thus, the door assemblies 20*a*, 20*b* may be actuated independently of one another or actuated substantially simultaneously to one another. In other words, in one or more modes of operation, the door assemblies 20*a*, 20*b* may be actuated independently, such as during a maintenance and/or cleaning mode where one door assembly 20*a* is in the closed position while the other door assembly 20*b* is in the open position. In one or more other modes of operation, such as in a procedure setup mode, the door assemblies 20a, 20b may be actuated simultaneously to open and/or close the door assemblies 20a, 20b.

In the illustrated embodiment of FIG. 5, the first door assembly 20a has been opened. To open the first door assembly 20a, the user may enter a command via the user interface 32. The control module of the console 12 may then transmit a command to the linear actuator 208a to retract the actuator rod 210a to open the first door assembly 20a. It is contemplated that if the first door assembly 20a is configured to move outward, the linear actuator 208a may extend the actuator rod 210a to open the first door assembly 20a. As can be seen in FIG. 5, the actuator rod 210a is shown in the retracted configuration within the housing 216a of the linear actuator 208a. As the actuator rod 210a is retracted, the second door attachment bracket 184a is rotated or pivoted about an axis that extends through the pin 112a and the drive hinge 116a to move the door assembly 20a into the loading bay 38 to the open configuration. As can be seen the drive hinge 116a of the first door assembly 20a is rotated about 90° from the closed configuration (see, for example, FIG. 2). To open the second door assembly 20b, the user may similarly enter a command via the user interface 32. The control module of the console 12 may then transmit a command to the linear actuator 208b to retract the actuator rod 210b to open the second door assembly 20b (see, for example, FIG. 3). It is contemplated that if the second door assembly 20b is configured to move outward, the linear actuator 208b may extend the actuator rod 210b to open the second door assembly 20b. As the actuator rod 210b is retracted, the second door attachment bracket 184b is rotated or pivoted about an axis that extends through the pin 112b and the drive hinge 116b to move the door assembly 20b to the open configuration. When open (FIG. 3) the drive hinge 116b of the second door assembly 20b is rotated about 90° from the closed configuration (see, for example, FIG. 2). In some cases, the door assemblies 20a, 20b may be opened individually to allow the interior surfaces of the door assemblies 20a, 20b to be cleaned.

In some cases, a command may be entered via the user interface 32 to open and/or close both door assemblies 20a, 20b at the same time (i.e., simultaneously). For example, in some embodiments, the door assemblies 20a, 20b may be opened at the same to load the pump/catheter assembly 14 into the carriage assembly and the door assemblies 20a, 20b may be closed at the same time to begin the procedure.

Figure 6:
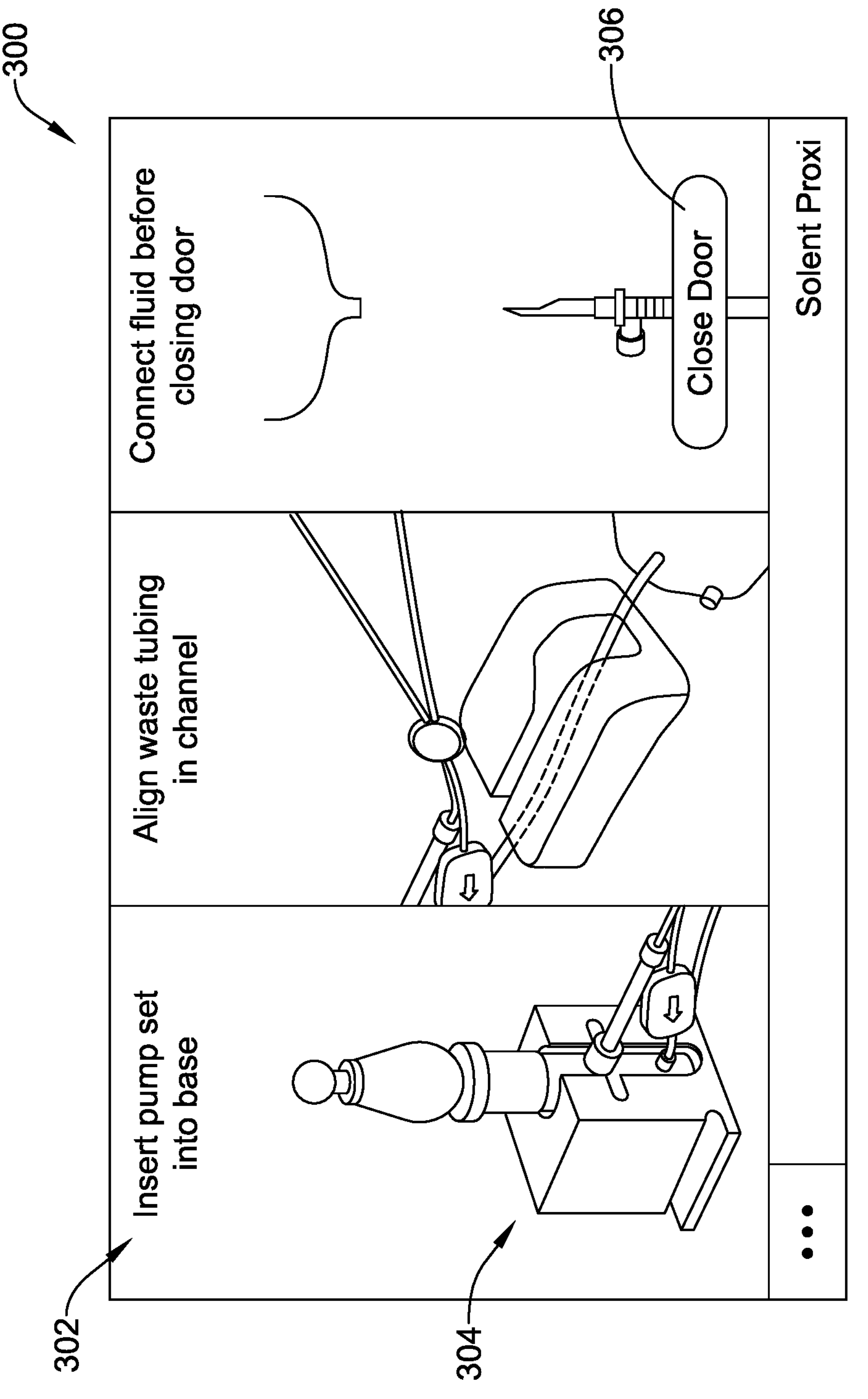
FIG. 6 is an illustrative control screen for operating the door assemblies of the thrombectomy console.

The user interface 32 may provide set-up and/or operational instructions to the user. FIG. 6 is a schematic view of an illustrative control screen 300 for setting up the thrombectomy system 10. For example, the control screen 300 may provide plain language instructions 302 and/or pictorial instructions 304 to assemble the pump/catheter assembly 14 with the console 12. Once the pump/catheter assembly 14 has been assembled with the console 12, the user may close the door assemblies 20a, 20b. This may be accomplished by actuation, for example, a "close door" button or region 306 on the control screen 300. The sensors, such as hall effect sensors or proximity sensors, may be used to determine if the door assemblies 20a, 20b have fully closed. If the door assemblies 20a, 20b do not fully close, a pop-up error or screen may be displayed on the user interface 32. After a predetermined length of time, the door assemblies 20a, 20b will reopen if the error is not cleared. In some cases, an additional pop-up or error screen may instruct the user to verify the path of the door assemblies 20a, 20b is clear. It is contemplated that the console 12 may be precluded from operating the pump/catheter assembly 14 until the door assemblies 20a, 20b are closed and in the closed position.

Once the door assemblies 20a, 20b are closed, the roller pump 40 may be closed. The actuator (not explicitly shown) may be lowered to engage the pump 56 of the pump/catheter assembly 14. It is contemplated that one or more steps of the set-up procedure may be prevented or locked out if the door assemblies 20a, 20b are not in the closed configuration. Once the set-up procedure is complete, the pump/catheter assembly 14 may be operated to remove thrombus, plaques, lesions, clots, etc. from veins or arteries. It is further contemplated that operation of the pump/catheter assembly 14 may be prevented if the door assemblies 20a, 20b are not in the closed configuration.

Figure 7:
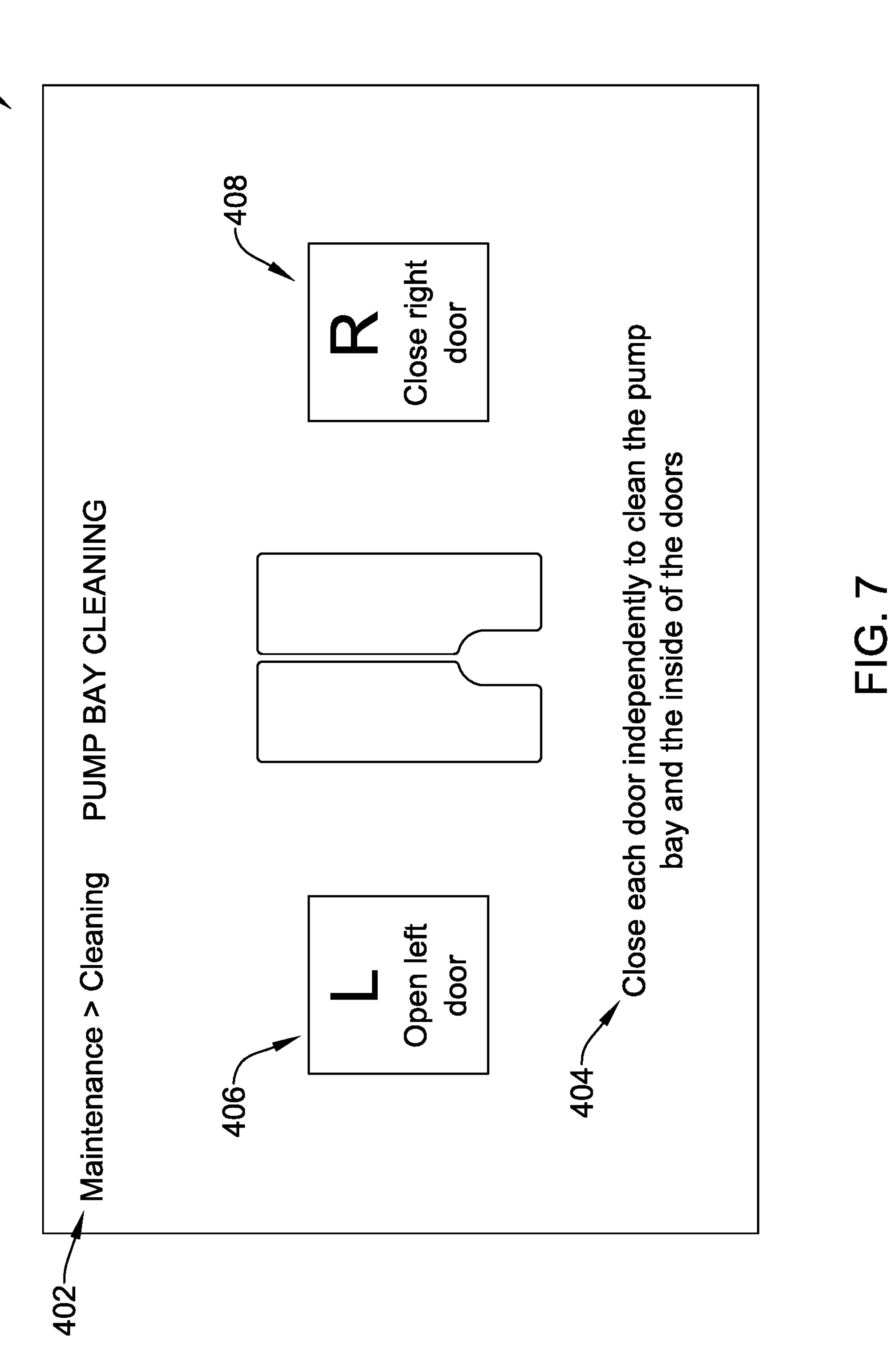
FIG. 7 is another illustrative control screen for operating the door assemblies of the thrombectomy console.

Once the procedure is complete, the user may use the user interface to enter a maintenance mode. FIG. 7 is a schematic view of an illustrative control screen 400 for cleaning the loading bay 38 after a procedure, or as otherwise necessary. For example, from a home screen, the user may first select a maintenance mode and once in the maintenance mode the user may select cleaning, as shown at the navigation tree 402. The user may be provided with plain language instructions 404. The control screen 400 may further include a first button or touch region 406 for closing the left or first door assembly 20a and a second button or touch region 408 for closing the right or second door assembly 20b. The user may select individual door assemblies 20a, 20b to allow the interior of the door assemblies 20a, 20b to be cleaned. It is contemplated that when a user selects one of the touch regions 406, 408 the opposite door assembly 20a, 20b will be closed. For example, if the user selects the first touch region 406 to open the first door assembly 20a, the second door assembly 20b may be closed if it is open.

It is contemplated that the user interface 32 may include additional control screens for setting up the thrombectomy system 10 and/or controlling the operation of the door assemblies 20a, 20b. In some examples, the user interface 32 may allow the user to adjust a speed at which the door assemblies 20a, 20b open. In some cases, the door assemblies 20a, 20b may be configured to open at a same speed. In other examples, the door assemblies 20a, 20b may be configured to operate at different speeds. It is contemplated that the speed at which the door assemblies 20a, 20b open and/or close may be based, at least in part, on how quickly the actuator rod 210a, 210b of the linear actuator 208a, 208b is moved.

The materials that can be used for the various components of the thrombectomy catheter, pump/catheter assembly, and/or other devices disclosed herein may include those commonly associated with medical devices. For simplicity purposes, the following discussion makes reference to the pump/catheter assembly and its related components. However, this is not intended to limit the devices and methods described herein, as the discussion may be applied to other similar devices, tubular members and/or components of tubular members or devices disclosed herein.

The various components of the devices/systems disclosed herein may include a metal, metal alloy, polymer (some examples of which are disclosed herein), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-clastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylenc (PP), polyvinylchloride (PVC), polyether-ester (for example, ARNITEL® available from DSM Engineering Plastics), ether ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of the pump/catheter assembly and its related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the pump/catheter assembly and its related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the pump/catheter assembly and its related components to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. A console for a thrombectomy system, the console comprising:

one or more panels enclosing an internal structure of the console;

at least one door assembly, the at least one door assembly movable between an open configuration configured to expose an interior of the console and a closed configuration configured to enclose the interior of the console;

a carriage assembly disposed within the interior of the console and accessible via the at least one door assembly, the carriage assembly configured to receive a pump/catheter assembly; and at least one linear actuator coupled to the at least one door assembly;

wherein linear movement of the at least one linear actuator is translated to rotational movement of the at least one door assembly;

wherein the at least one door assembly is configured to open inwardly into the interior of the console.

2. The console of claim 1, wherein the at least one first door assembly includes a first door assembly and a second door assembly, wherein both the first door assembly and the second door assembly are configured to open into the interior of console.

3. The console of claim 1, wherein the at least one door assembly is configured to rotate about an outer lateral side thereof.

4. The console of claim 1, wherein the at least one door assembly comprises a door panel and a first door attachment bracket, the first door attachment bracket coupled to a first end of the door panel.

5. The console of claim 4, further comprising a fixation member coupled to the first door attachment bracket, the fixation member configured to be rotatably coupled to a frame of the console.

6. The console of claim 4, further comprising a drive hinge coupled to a second end of the door panel.

7. The console of claim 6, wherein the drive hinge is coupled to a bell crank system, the bell crank system coupled to the at least one linear actuator.

8. The console of claim 7, wherein the bell crank system comprises a second door attachment bracket, an arm extending radially from the second door attachment bracket, and an actuator rod coupled to the arm.

9. The console of claim 1, further comprising at least one magnet disposed adjacent to a first end of the at least one door assembly.

10. The console of claim 2, wherein the at least one linear actuator comprises a first linear actuator coupled to the first door assembly and a second linear actuator coupled to the second door assembly.

11. The console of claim 2, wherein the first door assembly and the second door assembly are configured to be independently operated.

12. The console of claim 2, wherein the first door assembly and the second door assembly are configured to be simultaneously operated.

13. The console of claim 2, wherein when the first door assembly and the second door assembly are in the closed configuration, the first door assembly and the second door assembly define an opening configured to allow a portion of a pump/catheter assembly to pass therethrough.

14. The console of claim 1, further comprising a control panel.

15. The console of claim 1, wherein interior walls of the console include recesses sized and shaped to allow the at least one door assembly to be positioned therein when the at least one door assembly is in the open configuration.

16. A console for a thrombectomy system, the console comprising:

a plurality of panels enclosing an internal structure of the console, the plurality of panels including at least a floor panel;

a first door assembly comprising a first door panel, a first door attachment bracket of the first door assembly, and a magnet disposed within a cavity of the first door attachment bracket of the first door assembly;

a second door assembly comprising a second door panel, a second door attachment bracket of the second door assembly, and a magnet disposed within a cavity of the first second door attachment bracket of the second door assembly;

a first linear actuator coupled to the first door assembly, the first linear actuator separated from the internal structure of the console by the floor panel;

a second linear actuator coupled to the second door assembly, the second linear actuator separated from the internal structure of the console by the floor panel; and a carriage assembly disposed within an interior of the console and accessible via the first door assembly and the second door assembly, the carriage assembly configured to receive a pump/catheter assembly;

wherein the first linear actuator is configured to move the first door assembly between an open configuration configured to expose the interior of the console and a closed configuration configured to enclose the interior of the console and the second linear actuator is configured to move the second door assembly between an open configuration configured to expose the interior of the console and a closed configuration configured to enclose the interior of the console.

17. The console of claim 16, wherein the first linear actuator is coupled to the first door assembly via a first bell crank assembly and the second linear actuator is coupled to the second door assembly via a second bell crank assembly.

18. The console of claim 17, wherein the first bell crank assembly and the second bell crank assembly each comprise a second door attachment bracket, an arm extending radially from the second door attachment bracket, and an actuator rod coupled to the arm.

19. The console of claim 18, further comprising a first drive hinge extending between the first door panel and the first bell crank assembly and a second drive hinge extending between the second door panel and the second bell crank assembly.

20. A console for a thrombectomy system, the console comprising:

a housing enclosing an internal structure of the console;

a first door assembly comprising a door panel and a first door attachment bracket;

a second door assembly comprising a door panel and a second door attachment bracket;

a first linear actuator coupled to the first door assembly;

a first drive hinge extending from a first end coupled to a laterally outward corner of the door panel of the first door assembly to a second end coupled to the first linear actuator, wherein a portion of the first drive hinge extends through a floor of the housing;

a second linear actuator coupled to the second door assembly;

a second drive hinge extending from a first end coupled to a laterally outward corner of the door panel of the second door assembly to a second end coupled to the second linear actuator, wherein a portion of the second drive hinge extends through a floor of the housing; and a carriage assembly disposed within an interior of the console and accessible via the first door assembly and the second door assembly, the carriage assembly configured to receive a pump/catheter assembly;

wherein the first door assembly and the second door assembly are each movable between an open configuration configured to expose the interior of the console and a closed configuration configured to enclose the interior of the console; and wherein the first door assembly and the second door assembly are configured to be moved independently or simultaneously.

* * * * *